United States Patent

Hanaki et al.

[11] Patent Number: 6,155,683
[45] Date of Patent: Dec. 5, 2000

[54] OPHTHALMIC APPARATUS FOR PHOTOGRAPHING AN EYE TO BE EXAMINED

[75] Inventors: Hirohiko Hanaki, Gamagori; Miwako Torii, Toyohashi, both of Japan

[73] Assignee: Nidek Co., Ltd., Aichi, Japan

[21] Appl. No.: 09/280,969

[22] Filed: Mar. 30, 1999

[30] Foreign Application Priority Data

Mar. 31, 1998 [JP] Japan .................................. 10-125443

[51] Int. Cl.[7] .............................. A61B 3/14; A61B 3/10
[52] U.S. Cl. ........................................... 351/206; 351/221
[58] Field of Search .................... 351/206, 207, 351/208, 212, 221, 246

[56] References Cited

U.S. PATENT DOCUMENTS

| | | | |
|---|---|---|---|
| 4,812,033 | 3/1989 | Ishikawa | 351/208 |
| 5,202,708 | 4/1993 | Sasaki et al. | 351/206 |
| 5,270,924 | 12/1993 | Hideshima | 364/413.13 |
| 5,430,507 | 7/1995 | Nishio et al. | 351/208 |
| 5,694,197 | 12/1997 | Tsukada et al. | 351/206 |
| 5,757,462 | 5/1998 | Nanjo | 351/206 |
| 5,864,382 | 1/1999 | Soya et al. | 351/206 |

FOREIGN PATENT DOCUMENTS

| | | |
|---|---|---|
| 8-24226 | 1/1996 | Japan . |
| 9-131321 | 5/1997 | Japan . |
| 9-135813 | 5/1997 | Japan . |
| 10-33482 | 2/1998 | Japan . |

Primary Examiner—Georgia Epps
Assistant Examiner—Jordan M. Schwartz
Attorney, Agent, or Firm—Finnegan, Henderson, Farabow, Garrett & Dunner, L.L.P.

[57] ABSTRACT

An ophthalmic apparatus for photographing an eye to be examined having a photographing optical system for photographing the eye, the apparatus comprising a judging device for judging whether or not a picture image photographed by the photographing optical system satisfies a predetermined image requirement, an informing device for informing a result judged by the judging device.

6 Claims, 4 Drawing Sheets

OPHTHALMIC APPARATUS FOR PHOTOGRAPHING AN EYE TO BE EXAMINED

BACKGROUND OF THE INVENTION

1. Field of the Invention

The present invention relates to an ophthalmic apparatus for photographing an eye to be examined in order to use the photographed picture image in examining or analyzing a condition of the eye.

2. Description of Related Art

As for this kind of apparatus, one known example is an apparatus which optically cuts an anterior part of the eye with slit light and photographs a sectional image thereof with a photographing optical system provided in accordance with the Scheimpflug's principle. The photographed picture image is then analyzed to locate an opaque area in the crystalline lens or in the cornea, and also to find out its opacity degree.

The apparatus has a photographing mode for photographing and saving a picture image of the eye and also an analyzing mode for performing a predetermined image analysis of the picture image photographed and saved in the photographing mode. In the photographing mode, an examiner sets a photographing condition such as quantity of illumination slit light and the like, and then photographs the eye. After shifting to the analyzing mode, the examiner enters operation commands such as selecting analysis items, designating a range to be analyzed and the like. In accordance with these operation commands, the apparatus executes a predetermined analysis program thereby to calculate a result.

In order to obtain a highly reliable result through analyzing the photographed picture image obtained in the above-described manner, it is necessary that the photographing condition in the photographing mode such as quantity of light should be suitable so as to meet a predetermined requirement for analysis.

However, whether or not the photographed image satisfies the predetermined requirement for analysis can not be judged until the apparatus goes into the analyzing mode and executes the analysis program thereby to obtain the result. If it turned out that the photographed picture image does not satisfy the predetermined requirement for analysis, the analyzing mode has to be again shifted back to the photographing mode. Thereafter, the photographing condition is adjusted based on the result of analysis in order to start over the photography on the same eye again. This retake procedure requires many operations and time, thus work efficiency thereof is low. In addition, a long duration of time on the retake procedure imposes heavy burden on the examinee.

Furthermore, when dealing with a great number of examinees, it is usually the case that the photography on each examinee is carried out first and then the photographed picture images saved upon photographing are later analyzed all together. However, it is inconvenient not to find out whether retake is necessary until the analysis is done.

SUMMARY OF THE INVENTION

The present invention has been made in view of the above circumstances and has an object to overcome the above problems and to provide an ophthalmic apparatus with which an examiner can easily find out whether or not a photographed picture image is in a suitable condition for image analysis. Consequently, saving the picture image or retaking another picture image can be operated with efficiency.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus for photographing an eye to be examined having a photographing optical system for photographing the eye comprises judging device for judging whether or not a picture image photographed by the photographing optical system satisfies a predetermined image requirement, informing device for informing a result judged by the judging device.

As has been described above, according to the present invention, it takes comparatively short time to judge whether or not the picture image is in the suitable condition for the image analysis, and therefore, the retake procedure, if necessary, can be handled immediately. In addition, the photographing condition for the retake is automatically adjusted and thereby to reduce a waiting time as well as burden on the examinee. It is convenient, especially when dealing with a great number of examinees, to be able to obtain picture images in desirable conditions with efficiency.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
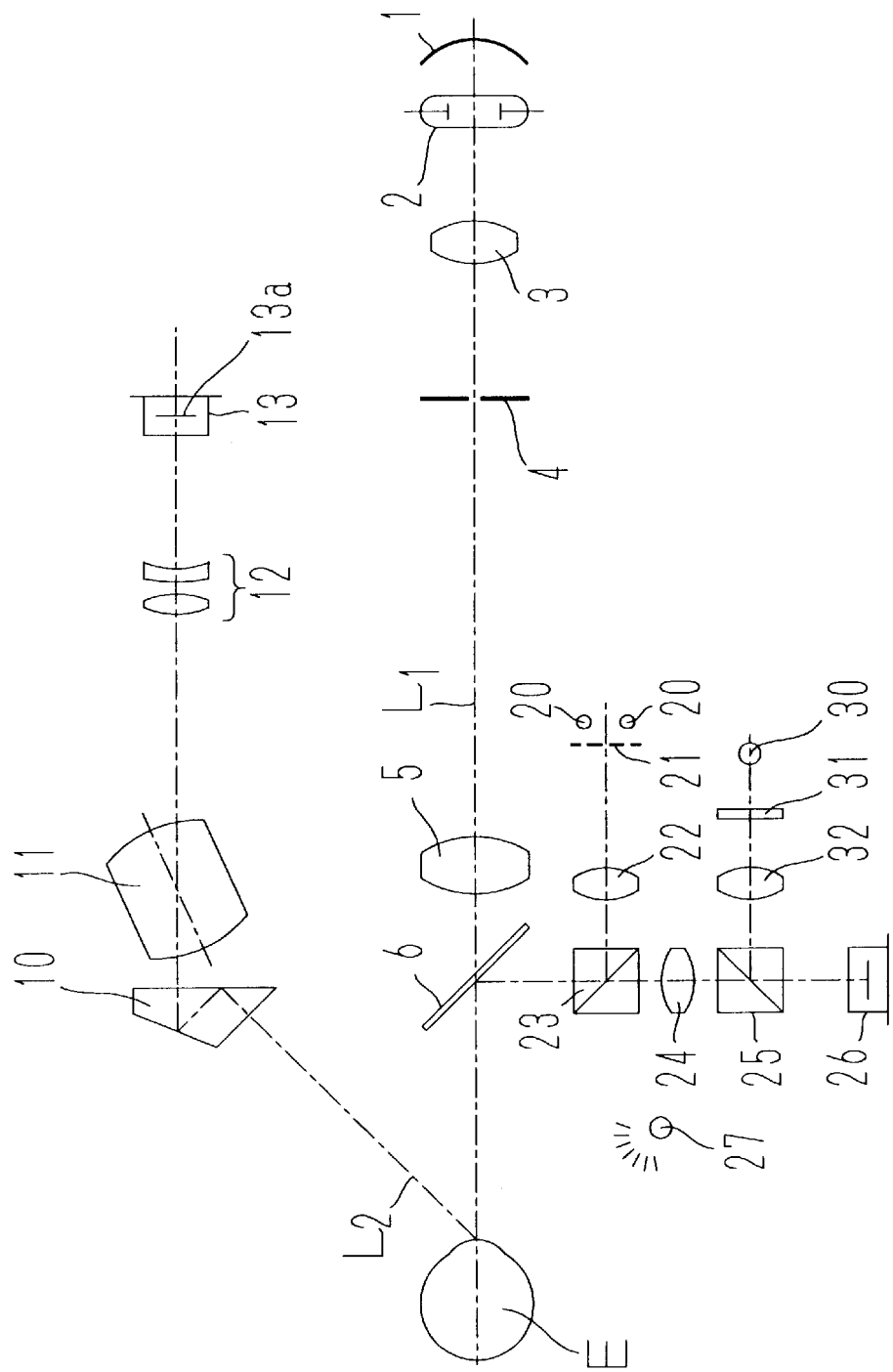
FIG. 1 is a view showing constructions of optical systems of a preferred embodiment of the present invention.

A detailed description of one preferred embodiment of an ophthalmic apparatus for photographing an eye to be examined embodying the present invention will now be given referring to the accompanying drawings. FIG. 1 is a view showing constructions of optical systems of a photographing analyzing apparatus, which photographs a cross section of an anterior part of the eye in order to analyze opacity degree of a cornea of the eye.

<Slit light projecting optical system>

Reference numeral 1 denotes a reflecting mirror, 2 is a flash lamp for photography, 3 is a condenser lens, 4 is a slit aperture diaphragm, 5 is a projecting lens, and 6 is a dichroic mirror which is disposed slantingly on an optical axis L1 of a slit light projecting optical system. The diaphragm 4 is a variable diaphragm of which slit can be lengthened or shortened, and the dichroic mirror 6 has characteristics of transmitting most of visible light but reflecting infrared light.

<Slit section photographing optical system>

Reference numeral L2 denotes a photographic optical axis of a slit section photographing optical system. 10 is a deflection angle prism to change a direction of the optical axis L2. 11 is a photographing lens, 12 is an anamorphic lens, 13 is a CCD camera for photographing a section. The optical axis L2 is disposed so as to intersect an optical axis L1 at an inclination angle of 45° near a corneal vertex when an alignment is almost completed by observing from in front. The lens 11 is arranged inclined to the optical axis L2 of which direction can be changed by the prism 10, so as to fulfil the Scheimpflug's principle. That is to say, the lens 11 is arranged so that, without the prism 10, an extension of an imaging plane 13a of the CCD camera 13 and an extension of a slit section of the anterior part of the eye E being optically cut by the slit illumination light would intersect on an extension of a principal plane of the photographing lens 11. According to this optical arrangement, a sectional image photographed by the CCD camera 13 (an image of a slit section formed around a collective point of the slit light by the scattered light from biomolecules of the anterior part of the eye) is allowed to hold a focal depth which focuses on the approximate entire sectional image.

<Alignment target projecting optical system>

Reference numeral 20 denotes a couple of light sources for alignment which project an alignment target from the front the eye E (a direction of a visual axis). The light sources 20 are also utilized as fixation light sources, and therefore emit infrared light which partially includes visible light. Each of the light sources 20 is disposed for a right eye and a left eye at positions where suitably correspond to inclinations of the visual axes of each eye. 21 is a target plate having pin-hole apertures along projection optical axes of the light sources 20, 22 is a projecting lens and 23 is a beam splitter. The target plate 21 is positioned near a front focal point of the projecting lens 21. Alignment light projected onto the eye E is reflected from the cornea in a manner of surface reflection, and thereby forming a target image of the target plate 21 at a distance equal to one half of a radius of a corneal curvature inwardly from a corneal vertex of the eye E.

<Front observing optical system>

Reference numeral 24 denotes a photographing lens, 25 is a beam splitter, and 26 is a CCD camera for observing a front side having its sensitivity within an infrared region. 27 is an infrared-illumination light source for illuminating the anterior part of the eye E. The image of the anterior part of the eye E illuminated by the infrared-illumination light source 27 is first reflected by the dichroic mirror 6, successively goes through the beam splitter 23, the lens 24 and the beam splitter 25 and then photographed by the CCD camera 26.

<Front reticle optical system>

Reference numeral 30 denotes a reticle plate illumination light source, 31 is a reticle plate in which an aiming mark is formed and 32 is a reticle projecting lens. The light source 30 illuminates the aiming mark formed in the reticle plate 31. After passing through the lens 32, the image of the aiming mark is reflected by the beam splitter 25 and then photographed by the CCD camera 26 along with the image of the anterior part of the eye and the target image.

Figure 2:
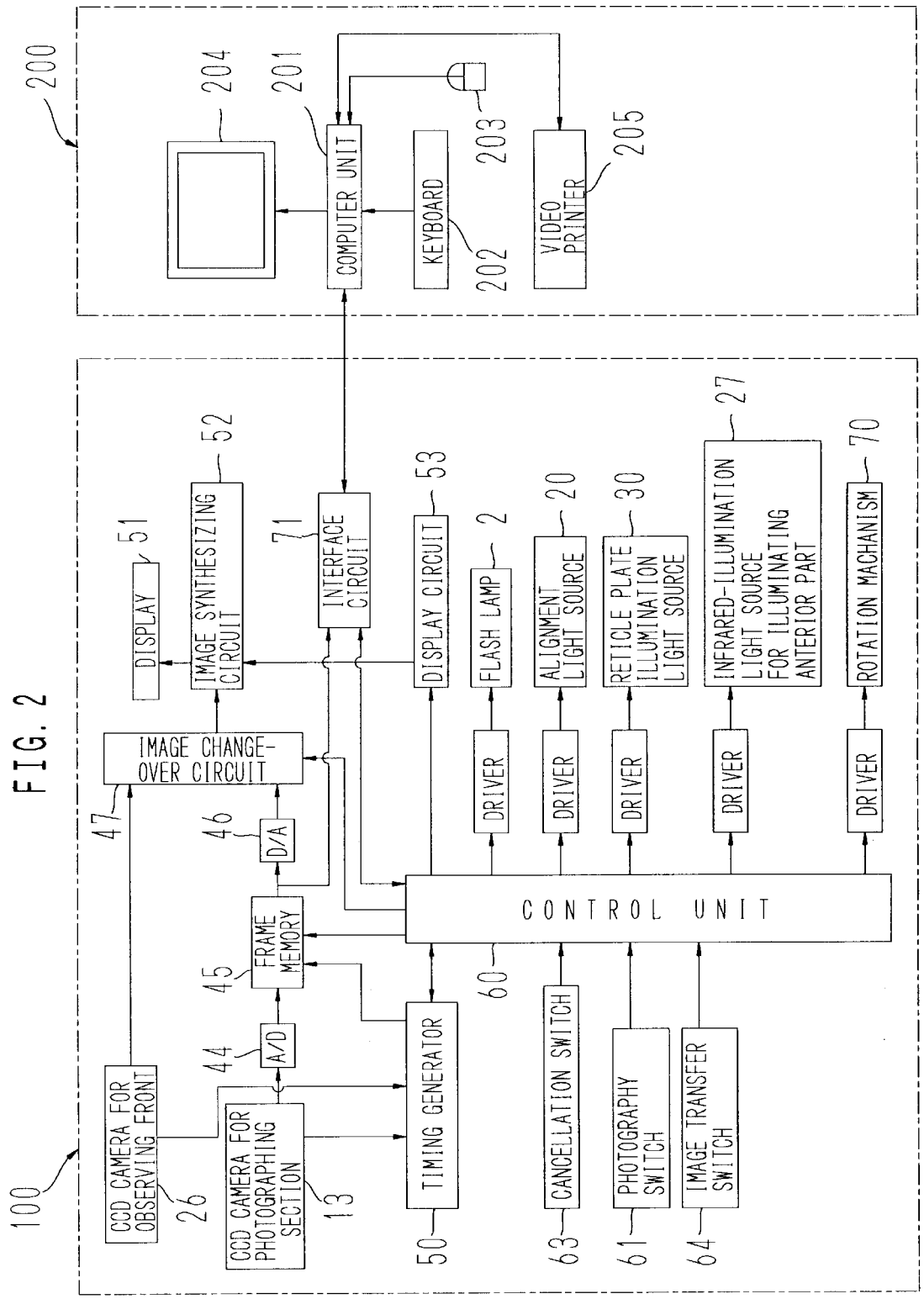
FIG. 2 is a view showing constructions of signal processing of a photographing unit 100 and of an image analyzing unit 200 in the embodiment of the present invention.

In the above-described optical systems, the slit section photographing optical system and the diaphragm 4 are structured so as to be rotated about the optical axis L1 by a rotation mechanism 70 (see FIG. 2). This allows the sectional image to be photographed at any desired angle. For this rotation mechanism, various known mechanisms may be applied. One example is to provide a gear for a housing which stores optical systems therein. Rotation is accomplished by a rotation pulse motor provided with a pinion which fits the gear.

FIG. 2 is a view showing constructions of a control system of the apparatus. The control systems of a photographing unit 100 and of an image analyzing unit 200 will be explained separately.

<Photographing unit>

A video signal from the CCD camera 13 is digitized by an A/D converting circuit 44 and then inputted to a frame memory 45 being synchronized with a signal generated by a timing generator 50. The picture signal inputted to the frame memory 45 is converted to a video signal by a D/A converting circuit 46 and then transmitted to an image change-over circuit 47. In response to a change-over signal from a control unit 60, the circuit 47 switches an image to be displayed on a display 51 between images taken by the CCD camera 13 and by the CCD camera 26. An image synthesizing circuit 52 synthesizes various information display generated by a display circuit 53 with the picture images inputted thereto so as to display on the display 51.

The sectional image of the anterior part of the eye which is frozen into the frame memory 45 upon photographing is transferred to the image analyzing unit 200 via an interface circuit 71 at an input from an image transfer switch 64.

The control unit 60 also controls adjustment of quantity of light that the flush lump 2 emits, as well as driving of the rotation mechanism 70 in accordance with a command signal carrying a photographing condition set in the analyzing unit 200.

<Image analyzing unit>

Reference numeral 201 denotes a computer unit which conducts image processing on pictorial data (image data) representing the sectional image inputted from the photographing unit 100 thereby making analysis. The computer unit 201 is provided with memory for saving the pictorial data and memory for storing an analysis program to carry out the image analysis therein. Input to the computer unit 201 can be made to set up the photographing condition such as the quantity of light that the flush lump 2 emits (Flush Level), the length of the slit upon photographing (Slit Length), a number (FILE No.), which is necessary upon saving the photographed picture image into the computer, the angle of the photographic axis (AXIS) and the like.

Reference numeral 204 denotes a color display which displays the picture image saved in the computer unit 201 and the result of analysis. A keyboard 202, a mouse 203 and the like are connected to the computer unit 201 to input operation commands. A video printer 205 which is capable of printing out the result of analysis along with the picture image is also connected to the computer unit 201.

Figure 3:
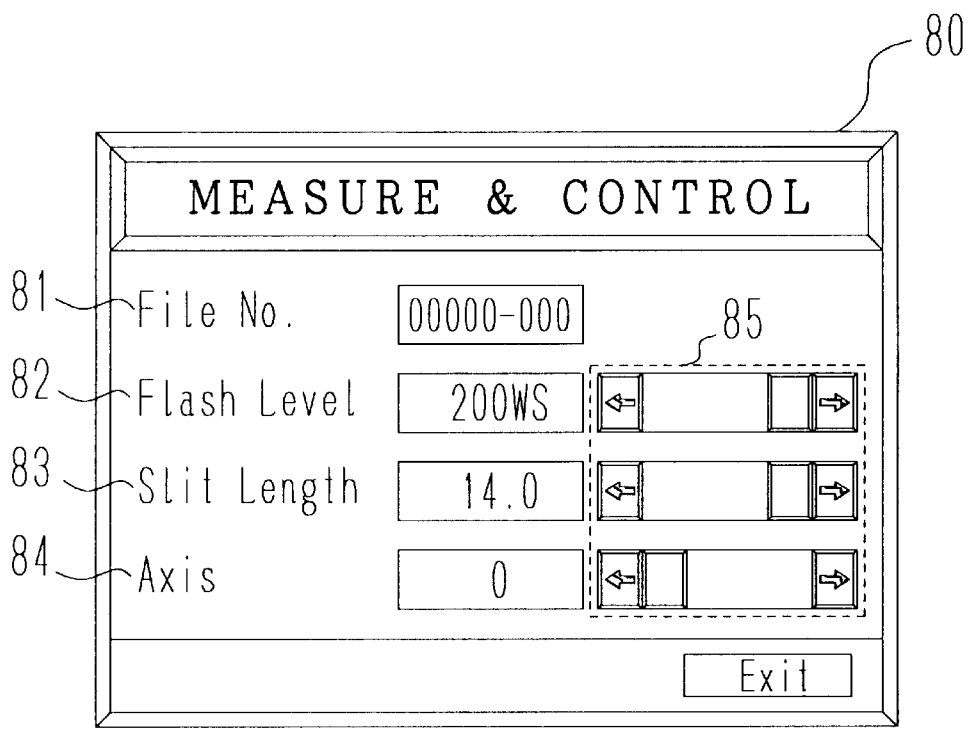
FIG. 3 is a view showing a photography control menu on a display.
Figure 4:
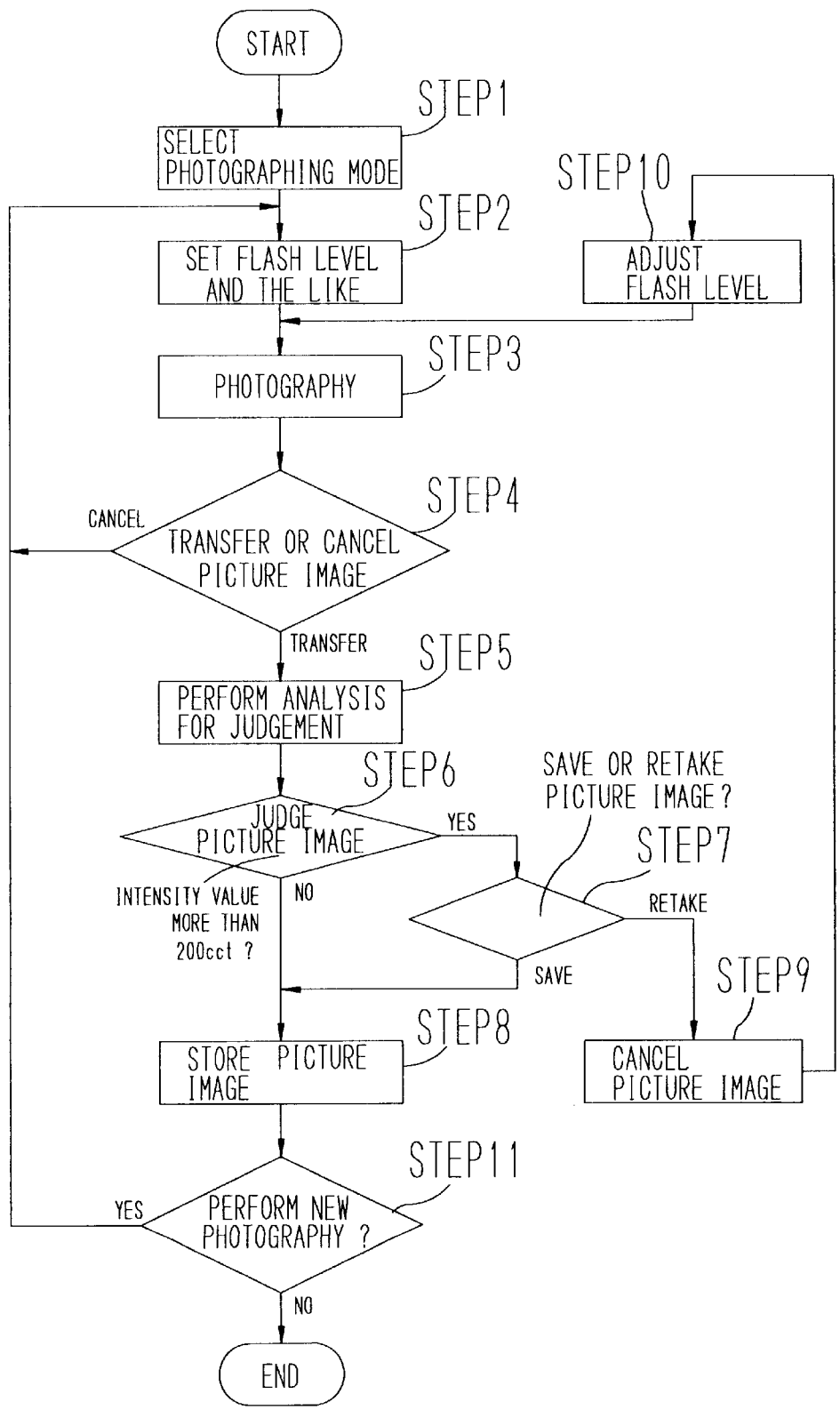
FIG. 4 is a flow chart showing a procedure upon photography.

Hereinafter, a description will be made regarding operations of the ophthalmic apparatus for photographing an eye to be examined having the above-described configuration with referring to the flow chart shown in FIG. 4. An examiner first selects a photographing mode with the mouse 203 from a main menu being displayed on the display 204, thereby to alternatively display a photography control menu 80 shown in FIG. 3 (STEP 1). Next, the examiner sets necessary condition by directly inputting letters and numbers in slots for FILE No. 81, Flash Level 82, Slit Length 83 and AXIS 84, or by selecting a photographing condition with scroll buttons 85 beside each slot. Brightness of the flush level 2 is divided into four levels: 200 WS, 150 WS, 100 WS and 50 WS. An appropriate level is selected in accordance with the opacity degree of the cornea of the eye (STEP 2).

After the photographing condition is all set, an eye of the examinee to be photographed is positioned at a predetermined position of the photographing unit 100 for carrying out the photography. To correct deviation between the visual axis and the optical axis, which allows the right eye and left eye to be photographed under the even condition, one of the two light sources 20 which corresponds to the eye being photographed is selectively lit. The eye being photographed is fixed to the target plate 21 provided in the alignment target projecting optical system, which at this time functions as the fixation optical system. The examiner moves a photographing optical system (the optical systems) provided in the photographing unit 100 in vertical and horizontal directions relative to the eye being photographed by operating an unillustrated joystick or the like and thereby making predetermined relationship between the alignment target image and the reticle (aimingmark) image. In addition, the photographing unit 100 is shifted in a back-and-forth direction to a point where the alignment target image becomes the smallest and clearest so as to accomplish alignment of a working distance.

When the two axes are brought into coincidence with each other by observing the front image and the alignment of the working distance is completed, the examiner depresses a photography switch 61. When the photography switch 61 is depressed, the control unit 60 makes the flush lump 2 flush, and thereby carrying out photography. Since the slit-section photographing optical system and the diaphragm 4 are being rotated by the rotation mechanism 70 in accordance with the photographic angle set up on the menu 80, a cross section can be photographed at an intended axial angle (STEP 3).

The corneal section which is cut optically by the silt illumination is photographed by the CCD 13 and the photographed picture image is frozen into the frame memory 45. The control unit 60 sends a change-over signal to the circuit 47, thereby switching a display screen on the display 51 to the sectional image being frozen in the frame memory 45. The examiner visually checks displacement of the sectional image and the like on the screen. If the picture image is satisfactory, the examiner depresses the image transfer switch 64, and if not, depresses a cancellation switch 63 (STEP 4).

In response to the input signal from the switch 64, the control unit 60 transfers the picture image of the corneal section to the computer unit 201 in the analyzing unit 200 via the circuit 71. The display 204 displays the picture image transferred thereto. When the photographed picture image is inputted from the photographing unit 100, the computer unit 201 judges whether or not the photographed picture image meets the requirement to carry out image analysis. The judgement is made in the following way. In the analyzing mode, intensity values which represent brightness of each pixel of the photographed picture image are divided into 256 levels ranging from 0 to 255 cct in order to carry out the image analysis. The opacity degree is analyzed based on the intensity values which are divided into these levels. Therefore, a judgement regarding the requirement for the analysis is made based on the intensity values.

First, the highest intensity value among the pixels along one scanning line of one picture image is detect. The detection is repeated on every scanning line sequentially. If an intensity value which exceeds a predetermined threshold intensity value (for example, 200 cct) is detected, the photographed picture image is then jugged not to meet the requirement for the analysis (STEP 5, STEP 6). This procedure allows to prevent the intensity value representing the peak intensity from exceeding the upper limit (255 cct) even in the cases where the opacity is in a developed stage. Accordingly, the result with relatively high reliability can be obtained.

Figure 5:
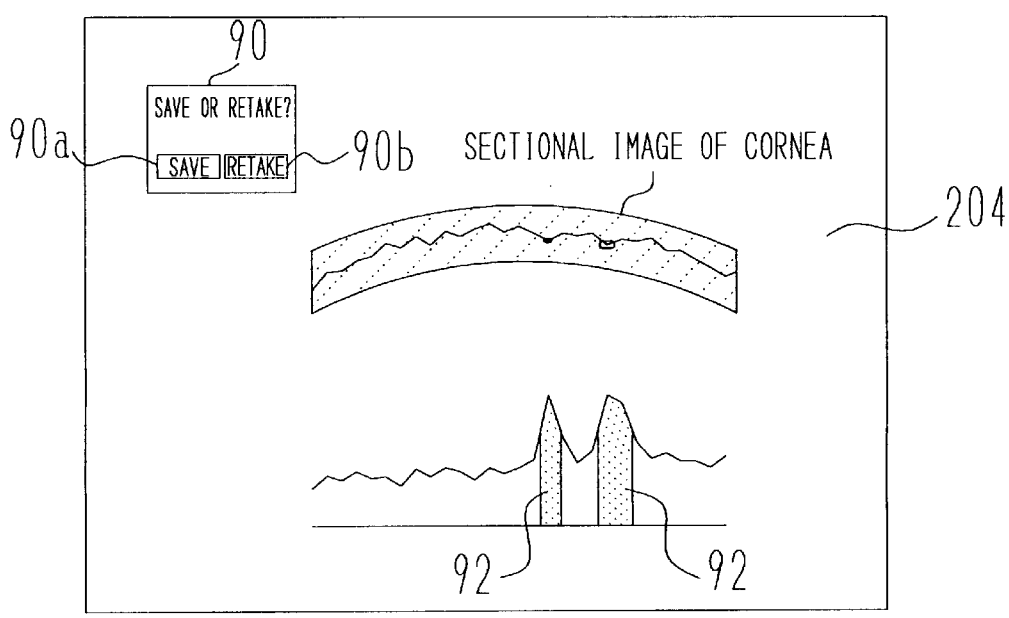
FIG. 5 is a view showing an example of a screen on the display.

If any of the detected intensity values exceeds the predetermined threshold intensity value, a confirmation menu 90 and a graph 91 are displayed on the display 204 along with the photographed picture image of the corneal section as shown in FIG. 5 (STEP 7). The confirmation menu 90 is utilized to select either to save or to abandon the photographed image, and the graph 91 shows a line which connects the intensity values detected along each scanning line. The menu 90 is displayed in a position to avoid blocking other information provided on the screen and a range 92 is indicated in the graph 91 to clearly show a range in which the intensity values exceed the threshold intensity value. With reference to the information provided on the screen, the examiner decides whether or not to save the photographed picture image and then depresses a SAVE button 90a to save the image, or a RETAKE button 90b to abandon the image (STEP 8, STEP 9).

At a click on the RETAKE button 90b, the computer unit 201 abandons the photographed picture image. Thereafter, the computer unit 201 reduces the brightness of the flush lump 2 by one flush level as preparation to carry out photography again under the same FILE No., Slit Length and AXIS (STEP 10).

At a click on the SAVE button 90a, on the other hand, the computer unit 201 saves the photographed image and then make preparation for photographing a new picture image (STEP 11).

If it is judged that the photographed picture image does not satisfy the requirement for analysis, the screen for confirmation, as shown in FIG. 5, may not have to be displayed. Instead, it may be possible to simply display that the photographed picture image does not meet the requirement, and then to automatically move on to the preparation for retake procedure.

On the other and, when it is jugged that the photographed picture image satisfies the requirement, the computer unit 201 automatically saves the photographed picture image and then make preparation for new photography.

As has been described above, an immediate check can be made, without shifting to the analyzing mode, as to whether or not the photographed picture image is in a desirable condition. Therefore, it requires a relatively short time even when photography has to be done again. In addition, since the photography condition upon the retake is automatically adjusted with reference to the condition of the picture image previously photographed, burden imposed on the examinee can be kept minimum. This also allows shorten time required in the retake procedure and thus the waiting time of the examinee is shortened as well.

When the photographed picture image is saved in the above-described manner, the photographing mode is then switched to the analyzing mode where analysis menus are selected to calculate the analysis. In the analyzing mode, it is obtained that the intensity values (density values which represent light and shade) of each pixel of the photographed picture image of the corneal section. Varies analyses are made all based on the intensity values. Referring to the analyses, the following are available. To visually capture the position of the opaque area and its opacity degree in the sectional image of the cornea, a horizontal direction and a vertical direction of the photographed image of the corneal section in FIG. 5 are respectively expressed by X and Y coordinates. The position of the peak intensity values along the X axis are displayed overlapping with the picture image of the corneal section together with a graph indicating the peak intensity values. In addition, by designating an intended range, the peak intensity value is integrated and shown graphically or all the intensity values on the scanning line are integrated and expressed numerically. As for the details of the analyses, see Japanese Patent KOKAI (unexamined application) Publication No. HEI 10-33482 corresponding to U.S. Pat. No. 5,864,382.

It should be understood that modifications may be made in the embodiment described above. One modification upon photographing a fondus of an eye to be examined, for example, is to set up a certain threshold level regarding intensity information about an obtained picture image or regarding coefficient of correlation between two picture images utilized for a stereophic image. The threshold level provides a standard upon deciding whether to save the picture image or to abandon the picture image and retake a new one.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus which is provided with a photographing optical system including a photoelectric photographing element for photographing an eye to be examined, the apparatus comprising:

alignment means for aligning the photographing optical system with the eye;

store means for storing a luminance threshold value which is set to perform significant luminance analysis on a photographed picture image of the eye which has been appropriately aligned by alignment means;

judging means for judging whether or not luminance of the photographed picture image exceeds the luminance threshold value through processing a picture signal transmitted from the photographing element; and instructing means for giving instructions to change light quantity for photographing when the judging means judges that the luminance of the photographed picture image exceeds the luminance threshold value.

2. The ophthalmic apparatus according to claim 1, further comprising picture image saving means for saving the photographed picture image for the purpose of analysis in response to a signal indicative of a judgment made by the judging means when the judging means judges that the luminance of the photographed picture image does not exceed the luminance threshold value.

3. The ophthalmic apparatus according to claim 1, further comprising selecting means which is used by a photographer for selecting whether to save or to cancel the photographed picture image when the judging means judges that the luminance of the photographed picture image exceeds the luminance threshold value, and wherein the instructing means gives instructions to change the light quantity for photographing when cancellation of the photographed picture image is selected by using the selecting means.

4. The ophthalmic apparatus according to claim 1, further comprising:

an illumination light source for illuminating the eye upon photographing; and controlling means for controlling the illumination light source, and wherein the instructing means instructs the controlling means to generate a control signal for adjusting light quantity of the illumination light source such that the luminance of the photographed picture image does not exceed the luminance threshold value.

5. The ophthalmic apparatus according to claim 1, wherein the photographing optical system includes an optical system for photographing a cross section of an anterior part of the eye.

6. The ophthalmic apparatus according to claim 1, further comprising an observing optical system including a display for displaying a front image of the anterior part of the eye thereon, and wherein the photographed picture image is displayed on the display.

* * * * *